United States Patent [19]
Visser et al.

[11] Patent Number: 5,698,203
[45] Date of Patent: Dec. 16, 1997

[54] EUROPEAN VACCINE STRAINS OF THE PORCINE REPRODUCTIVE RESPIRATORY SYNDROME VIRUS (PRRSV)

[75] Inventors: Nicolaas Visser; Petrus Alphonsus Maria Van Woensel, both of Boxmeer, Netherlands; Volker Ohlinger, Havixbeck; Emilie Weiland, Ammerbuch, both of Germany

[73] Assignee: Akzo Nobel N.V., Arnhem, Netherlands

[21] Appl. No.: 419,781

[22] Filed: Apr. 11, 1995

[30] Foreign Application Priority Data

Apr. 11, 1994 [EP] European Pat. Off. ............ 94200964

[51] Int. Cl.$^6$ .................... C12N 7/02; A61K 39/155
[52] U.S. Cl. .......... 424/218.1; 435/7.1; 435/236; 435/239; 530/388.3; 530/389.4
[58] Field of Search ................. 424/218.1, 147.1; 530/388.3, 390.1, 389.4; 435/236, 239, 7.1

[56] References Cited

FOREIGN PATENT DOCUMENTS

| 21375 | 12/1992 | WIPO. |
|---|---|---|
| 03760 | 3/1993 | WIPO. |
| WO 93/06211 | 4/1993 | WIPO. |
| WOA 9307898 | 4/1993 | WIPO. |

OTHER PUBLICATIONS

J.M.A. Pol et al., *The Veterinary Quaterly*, 13:3:137–143, 1991.

G. Terpstra et al., *The Veterinary Quaterly*, 13:3:131–136, 1991.

E. Nelson et al., "Differentiation of US and European isolates of porcine reproductive and resiratory virus by monoclonal antibodies," *J. Clin. Micro.*, 31:12:3184–3189, 1993.

H. Mardassi et al., "Identifications of major differences in the nucleocapsid proteins of Quebec strain and European strains of PRRSV," *J. Gen. Virol.*, 75:3:681–685, 1994.

G. Wensvoort et al., "Antigenic comparison of Lelystad virus and swine infertility and respiratory syndrome firus," *J. Vet. Diagn. Invest.*, 4:134–138, 1992.

J. Meulenberg et al., "Lelystad virus the causative agent of porcine epidemic abortion and respiratory syndrome" *Virology*, 192:62–72, 1993.

Paul, WE Fundamental Immunology p. 242 Third ED. 1993.

*Primary Examiner*—Lila Feisee
*Assistant Examiner*—Julie E. Reeves
*Attorney, Agent, or Firm*—Mary E. Gormley; William M. Blackstone

[57] ABSTRACT

The present invention is concerned with European strains of the Porcine Reproductive Respiratory Syndrome (PRRS) virus, which are attenuated, and show a characteristic reaction pattern with two monoclonal antibodies against wild-type PRRSV.

The invention also relates to vaccines for the protection of pigs against PRRS, to monoclonal antibodies reactive with PRRS virus and monoclonal antibodies specifically non-reactive with the attenuated strains.

8 Claims, 2 Drawing Sheets

FIG. 2

EUROPEAN VACCINE STRAINS OF THE PORCINE REPRODUCTIVE RESPIRATORY SYNDROME VIRUS (PRRSV)

FIELD OF THE INVENTION

The present invention is concerned with European strains of the Porcine Reproductive Respiratory Syndrome (PRRS) virus, vaccines for the protection of pigs against PRRS, monoclonal antibodies reactive with PRRS virus and monoclonal antibodies specifically non-reactive with the attenuated strains.

BACKGROUND OF THE INVENTION

In 1987, a then unknown disease in pigs was detected in North America, from where it later spread to Canada (Hill, H.; In: Proceedings of the Mystery Swine Disease Committee meeting, Oct. 6, 1990, Denver, Col., Livestock Conservation Institute, Madison Wis., USA., Keffaber et al; Am. Assoc. Swine Pract. Newsletter 1:1–9 (1989)). The disease, which was characterised by the fact that it induced both abortion and respiratory disease, was first called Mystery Swine Disease (MSD). Nowadays, in America and Canada, the disease is also known as Swine Infertility and Respiratory Syndrome (SIRS).

Since 1990, the disease has been found in Europe, where it first caused outbreaks in Germany, followed by outbreaks in the Netherlands and Belgium, and the disease is now spreading through Europe. In Europe, the disease is commonly known as Porcine Reproductive Respiratory Syndrome (PRRS), and as Porcine Epidemic Abortion and Respiratory Syndrome (PEARS). The disease is now referred to as PRRS, worldwide.

The pathology is not restricted to abortion and respiratory disease. Other symptoms, usually or occasionally seen with the disease are: reduced appetite, anorexia, and bluish discolorations of the extremities, especially the ears.

The causative agent of the disease is now known to be a small enveloped RNA virus, and the European type of this virus has been described by Wensvoort et al. (The Vet. Quarterly; 13:121–130 (1991)). Its relatedness to Lactate Dehydrogenase-elevating virus (LDV) and Equine Arteritis virus has been described by Conzelmann et al. (Virology 193:329–339 (1993)) and by Meulenberg et al. (Virology 192:62–72 (1993), thus placing the virus in the group of Arteriviridae.

A strain of this European type, called the "Lelystad Virus" (LV) has been deposited with the Institut Pasteur, Paris, France under accession number I-1102, in connection with PCT WO 92/21375 by the Central Veterinary Institute, Lelystad, The Netherlands.

Another European strain has been described in EPA no. 91,202,646.5, and was deposited with the Collection Nationale de Cultures de Microorganismes (CNCM) of the Institut Pasteur at Paris France under accession number I-1140. This European strain has recently been described by Conzelmann et al. (Virology 193:329–339 (1993)).

The American type of the virus has been described by Benfield et al. (J. Vet. Diagn. Invest. 4:127–133 (1992)). A strain of the American type has been deposited with the ATCC under accession number VR-2332, and is mentioned in PCT WO 93/03760 and European Patent Application 0,529,584

An important observation was made by Wensvoort et al. (J. Vet. Diagn. Invest 4: 134–138 (1992), soon after the virus was found, when he compared American and European strains on the basis of their antigenic characteristics.

He raised sera against both the American type (as e.g. the strain deposited with the ATCCVR-2332 as mentioned above) and the European type (as e.g. the strain deposited with the Institut Pasteur, Paris, France under accession number I-1102) in several pigs, and compared the cross-reactivity of the anti-European (LV) and anti-American (VR-2332) sera with three American virus isolates and 4 European isolates.

As disclosed by Wensvoort et al. (J. Vet. Diagn. Invest 4: 134–138, 1992), sera against PRRS viruses of the European serotype are significantly less reactive with American isolates than with European isolates.

Even more surprising, sera raised against viruses of the American serotype are less reactive, or even not reactive at all, with European virus isolates.

Wensvoort et al. (J. Vet. Diagn. Invest 4:134–138 (1992) also shows the reactivity of sera raised against European and American isolates with the two reference viruses IP I-1102 (European) and ATTC VR-2332 (American). These results are even more striking: sera raised against European strains are not reactive at all with the American strain.

Thus, at that moment in time, for the first time it became unequivocally clear that two fully different serotypes of the virus exist: the American and the European serotypes.

Recently, Nelson et al. (74th Annual Meeting of the Conference of Research Workers in Animal Diseases, Nov. 8–9, 1993) and Mardassi et al. (74th Annual Meeting of the Conference of Research Workers in Animal Diseases, Nov. 8–9, 1993) showed it to be very easy to discriminate between European and American strains on the basis of these serological differences, by using monoclonal antibodies selectively reactive with one of the two serotypes.

The conclusion is that there is a recognized difference between American and European isolates, on the basis of their serotype. It also shows that it is possible to easily discriminate between American and European serotypes.

In addition to serological differences, there is a growing amount of evidence for large differences in nucleic acid sequences, when comparing the genomes of the American and the European serotypes.

Recently, more nucleic acid sequence data have become available, amongst which are sequences of various genes of various isolates.

Nelson et al. (74th Annual Meeting of the Conference of Research Workers in Animal Diseases, Nov. 8–9, 1993) demonstrated large differences between the nucleotide sequences of the genes coding for the nucleoprotein of the American and European serotypes. Since the nucleoprotein is an internal viral protein, it will not be prone to selective pressure. Thus it is surprising to find these differences. Nelson et al. used these nucleotide sequence differences for a PCR-based test for the discrimination between American and European strains.

In another recent paper, Katz et al. (74th Annual Meeting of the Conference of Research Workers in Animal Diseases, Nov. 8–9, 1993) compared sequences of polymerase-encoding genes of various isolates. There is hardly or no evolutionary pressure on polymerase genes in general. This also holds true for the polymerase genes of e.g. strains of the American serotype, as can be seen from the fact that there is a 87–95% homology within the American group. Therefore, it is surprising that a homology as low as 64–67% based on nucleic acids was found between European serotypes and American serotypes.

Mardassi published comparable results at the Conference mentioned above, showing that the 3'-terminal 530 nucleic acids of the Quebec PRRS Reference strain and European isolates only show a homology as low as 59%.

The results from the papers mentioned above make it most likely that the American and European serotypes diverged a long time ago, which would then easily explain their genetic differences and their serological unrelatedness.

In conclusion, there is a clear difference between American and European isolates, both on the basis of their overall nucleic acid sequence and their serotype. It also shows that it is possible to easily discriminate between American and European serotypes.

One other conclusion, however, is that on the basis of these findings it may well be impossible to find a universally applicable attenuated strain providing protection against infection with both American serotype strains and European serotype strains.

An attenuated strain of the American serotype has been described in European Patent Application 0,529.584. This strain is directly derived from the deposited American VR-2332 strain.

Therefore, animals vaccinated with this strain will not develop antibodies reactive with European strains.

This clearly means that in order to make a vaccine against European serotypes, an attenuated strain of the European serotype is desired.

SUMMARY OF THE INVENTION

The present invention for the first time provides attenuated strains of the European serotype.

Viruses of the European serotype are characterised in that they react to a higher titre in an Immunoperoxidase Monolayer Assay with a panel of antisera against the European PRRS virus LV (CDI-NL-2.91; as deposited with the Institut Pasteur under I-1102) compared with a reaction with a panel of antisera against the American PRRS virus SIRSV (ATCC VR-2332).

If a panel of sera is used, obtained about 40 days post-infection and from different animals, any virus can easily be classified as belonging either to the American or European serotype. Typically, the reactivity of a European strain with a panel of antisera against other European strains is about 400 times higher than with a panel of antisera against American strains. When a European strain is reacted with antisera against the deposited European strain I-1102 and the deposited American strain VR-2332, a typical difference in reactivity of about 55 times is found (Wensvoort et al. (J. Vet. Diagn. Invest 4: 134–138 (1992).

The attenuated strains according to the present invention are reactive with monoclonal antibodies produced by hybridoma A27 (deposited with Institut Pasteur at Paris France under accession number I-1401). These antibodies recognise the nucleoprotein of European serotype strains.

Attenuated strains of the European serotype have been found, but these still have an unacceptable level of virulence (such as I-1389, mentioned in the present invention).

The surprising characteristic of the viruses of the present invention is that they are no longer virulent, yet are able to induce a protective immune response. These viruses are characterised in that they are not recognised by monoclonal antibodies produced by hybridoma A35 (deposited with the Institut Pasteur at Paris France under accession number I-1402), which are reactive with ORF-4 of virulent PRRS viruses. (The open reading frames are described by, inter alia, Conzelmann et al. (Virology 193:329–339 (1993) and Meulenberg et al. (Virology 192:62–72 (1993)).

BRIEF DESCRIPTION OF THE DRAWINGS

Figure 2:
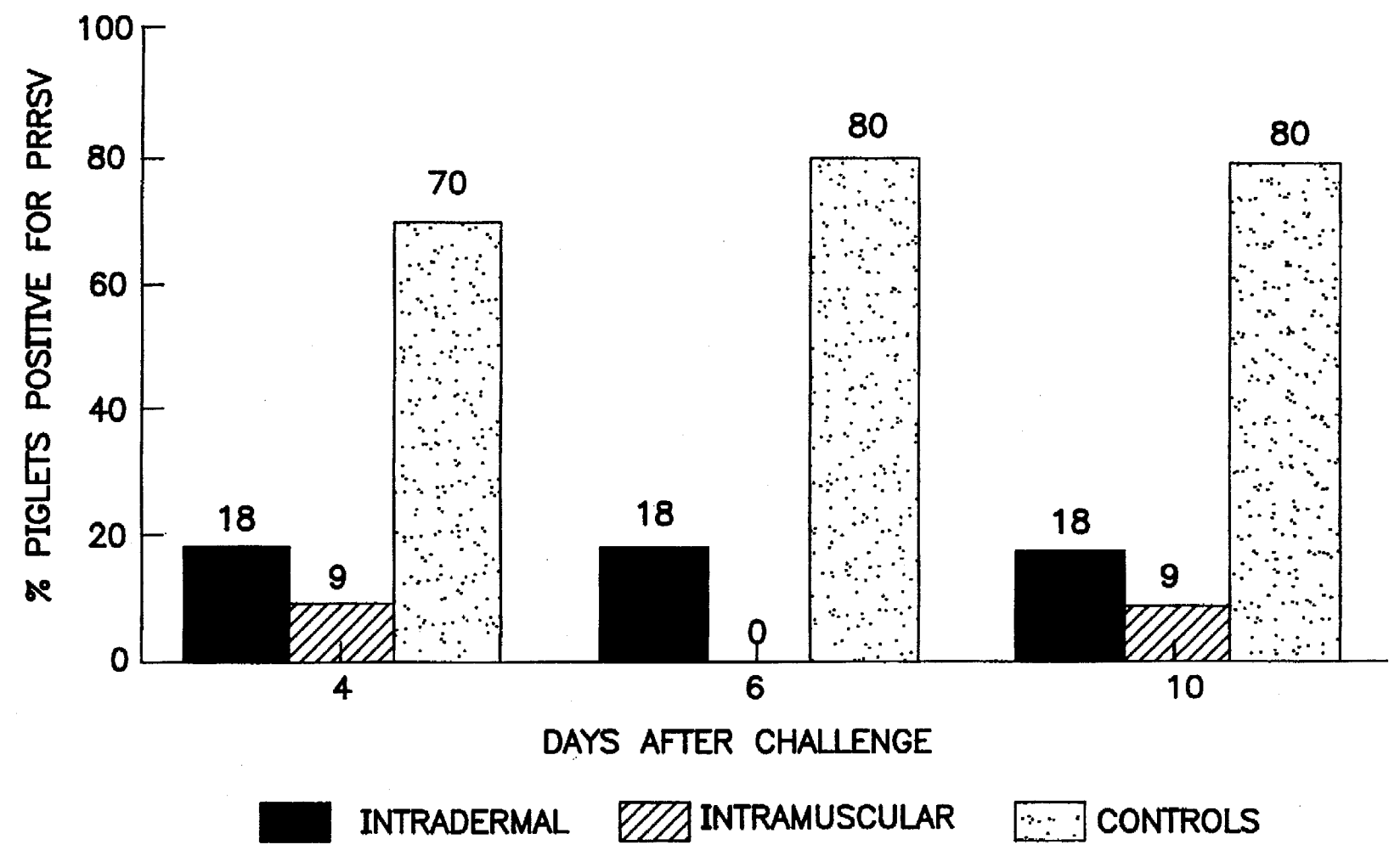

FIG. 2 shows the percentage of piglets positive for virus-isolation from the blood at 4, 6 and 10 days after challenge.

DETAILED DESCRIPTION OF THE INVENTION

Figure 1:
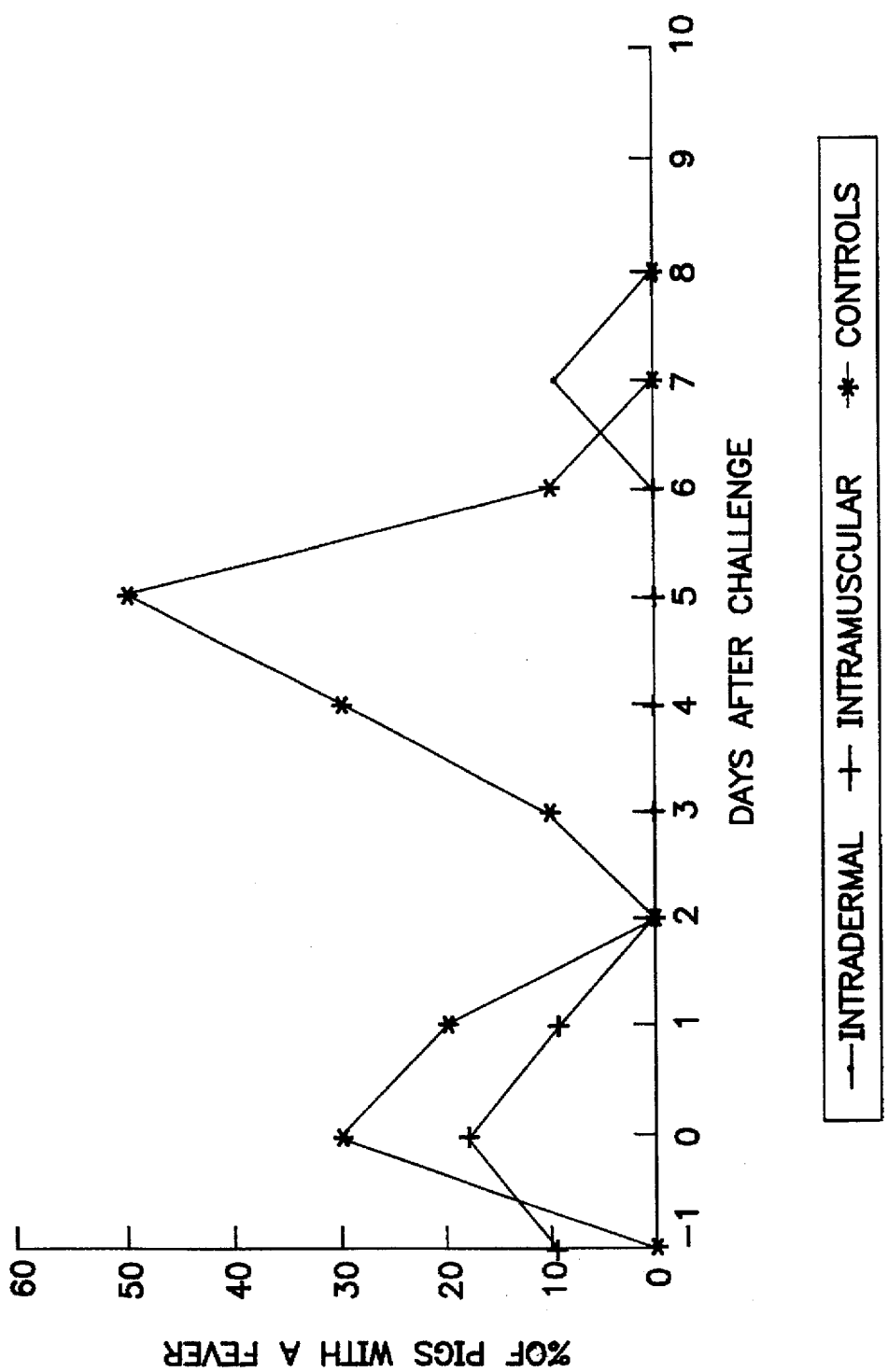
FIG. 1 shows the percentage of piglets per group with a fever (temperature above 40.5° C.) scored from one day before to eight days after challenge.

Examples of attenuated strains of the European serotype with a A35 serotype according to the present invention are the virus strains PRRS C and PRRS D, as deposited with the Collection Nationale de Cultures de Microorganismes (CNCM) of the Institut Pasteur at Paris, France, under the Accession number I-1387 (Strain D) and number I-1388 (Strain C).

These two deposited strains are merely examples of the strains that are embodied in the present invention.

Other European PRRS virus strains, also reactive with monoclonal antibody A27 and not reactive with A35 are also part of the invention.

These strains can be found, for example, by screening in the field for animals infected by PRRSV, isolation of the PRRS virus strain and subsequently testing for reactivity with both A35 and A27 antibodies.

Also part of the invention are virus strains derived from one of the deposited strains. For example, strains can be derived from one of the deposited strains by further passing of one of the deposited strains on cells in a suitable culture medium. Further passages can also be obtained by passing one of the deposited strains in an animal.

Also embodied in the present invention are vaccines, comprising a PRRS virus strain of the present invention. In these vaccines the virus according to the invention can be present as a live attenuated virus. One advantage of the use of live virus vaccines is that only a limited number of viruses has to be administered, since live viruses are self-replicative; typically, $10-10^7$ particles per dose can be used. Another advantage of a live virus vaccine is that it mimics the natural infection and therefore triggers the immune system in the natural way.

Vaccines can also be made by using the viruses of the present invention in an inactivated form. The advantage of this approach is that an inactivated virus is always fully safe, since it can never return to a virulent form. A vaccine based on inactivated viruses typically may contain the equivalent of $10^3-10^{10}$ live virus particles measured before inactivation. In general, inactivation can be achieved by chemical or physical means. Chemical inactivation can be effected by treating the virus with, for example, formaldehyde, β-propiolactone, ethylene-imine or a derivative thereof, an organic solvent (such as TWEEN (detergent), TRITON X (detergent), sodium deoxycholate, sulphobetain or octyl trimethylammonium salts. Examples of physical means of virus inactivation are heat and energy-rich radiation, e.g. UV light, X-radiation or gamma-radiation.

The vaccine according to the present invention may comprise a pharmaceutically acceptable carrier. One possible carrier is a physiological salt solution. Another pharmaceutically acceptable carrier is, for instance, the solution in which an adjuvant is provided.

Usually an adjuvant and, if desired, one or more emulsifiers such as TWEEN and SPAN (detergent) are also incorporated in the live or inactivated vaccine according to the invention. Suitable adjuvants are, for example, vitamin E acetate solubilisate, aluminium hydroxide, -phosphate or -oxide, (mineral) oil emulsions such as BAYOL and MARCOL52, and saponins. Incorporation of the antigens in Iscoms is also a possible way of adjuvation.

It is advantageous to add a stabilizer to live or inactivated viruses, particularly if a dry composition of live viruses is prepared by lyophilization. Suitable stabilizers are, for example, SPGA (Bovarnik et al., J. Bacteriology 59, 509, 1950), carbohydrates (such as sorbitol, mannitol, trehalose, starch, sucrose, dextran or glucose), proteins (such as albumin or casein), or degradation products thereof, and buffers (such as alkali metal phosphates). If desired, one or more compounds with adjuvant activity as described above can also be added.

A vaccine according to the invention may be administered by intramuscular or subcutaneous injection or via intranasal, intratracheal, oral, cutane, percutane or intracutane administration.

The vaccine according to the invention can be administered to pigs depending on the vaccination history of the sows at 1, 5 or 10 weeks of age, to sows before mating and/or 4–6 weeks before farrowing (booster vaccination), or to boars every half a year (boosters).

Vaccines according to the present invention may contain combinations of the PRRS component and one or more unrelated porcine pathogens, such as *Actinobacillus pleuropneumonia*, Pseudorabies virus, Porcine influenza virus, Porcine parvovirus, Transmissible gastroenteritis virus, rotavirus, *E. coli*, *Erysipelo rhusiopathiae*, *Pasteurella multocida*, and *Bordetella bronchiseptica*.

Although a vaccine according to the invention may be derived from any PRRS virus isolate of a European serotype, preferably the vaccine is derived from PRRS strains C or D, deposited at the Institut Pasteur at Paris France under accession number I-1388 or accession number I-1387.

Next to the use of whole live or inactivated virus preparations for vaccine purposes, the use of vital antigens for the preparation of vaccines is possible. The use of viral antigens, either as a crude preparation or in a more purified form, has the advantage that unwanted or unnecessary compounds from viral or cellular origin can be eliminated. This approach leads to vaccines with a low non-specific antigenic load, and thus to vaccination without undesired side effects.

Crude virus preparations can be purified to select for one or more viral antigens in a number of different ways known in the art. Purification can be done by centrifugation, molecular sieve chromatography, ion-exchange chromatography, chromatography over a column coated with specific antibodies, gel electrophoresis, etc.

A method for the preparation of PRRS viral antigen useful to be incorporated into a vaccine according to the invention includes the following steps:

a) inoculating susceptible tissue culture cells with the PRRS virus, b) cultivating the cells, and c) harvesting the viral antigen from the culture.

Preferably, the PRRS virus is cultured to high titres, i.e. at least $10^{6.0}$ TCID$_{50}$/ml.

For the production of the live attenuated viruses according to the invention, a number of methods known in the art for this purpose are available, e.g. adaptation of a specific PRRS virus isolate to grow in embryonated eggs or to a culture containing porcine tissue cells or other susceptible tissue cells or eggs, after which the virus is multiplied and harvested by collecting egg material or the tissue cell culture fluids and/or cells. Adaptation to growth at different temperatures may also be part of the attenuation process.

Optionally, during harvesting the yield of the viruses can be promoted by techniques which improve the liberation of the infective particles from the growth substrate, e.g. sonication.

Viral antigen to be incorporated into a vaccine according to the invention can be prepared by the growth of the PRRS virus isolates on macrophages (alveolar, peritoneal, peripheral, bone marrow or from any other site). Also, other cells with macrophage-like properties are useful, like promonocytes, monocytes, brain vascular endothelial cells and microglial cells. The macrophage or macrophage-like cells may be of SPF (specific pathogen free) or non-SPF origin (e.g. from regular commercial pigs). In the latter cases, precautions are taken for undesired contamination, e.g. by the use of proper antibiotics in the culture.

In addition, other known susceptible host cells can be used for this purpose.

Another route which can lead to a very useful procedure of virus growth is the establishment of a macrophage cell line. A number of possibilities which can lead to such desirable macrophage cell lines are outlined below.

Immortalization of macrophages can be done using conditioned medium of L(929) cells, SK6, ST, Vero or BHK cells. In these conditioned media at least the presence of lymphokines like the macrophage Colony Stimulating Factor (CSF) is of importance (Stanley, E. R., Methods Enzymology 116, 564–587, 1985).

Treatment of macrophages of any source with chemicals to invoke immortalization, e.g. β-propiolactone as an example of an alkylating agent that effects DNA metabolism can be used (Logrippo, G. A. and Harman, F. W., J. Immunol. 75, 123–128, 1955).

Also incorporated in the present invention are monoclonal antibodies produced by the hybridomas A27 and A35, as deposited with the Collection Nationale de Cultures de Microorganismes (CNCM) of the Institut Pasteur at Paris France under accession number I 1401 and accession number I 1402, respectively.

Antibodies reactive with the PRRSV antigenic determinant which is recognized by the monoclonal antibodies of the deposited hybridomas are also part of the invention.

EXAMPLE 1

Isolation of PRRS virus strains

Pigs in several countries in Europe were on a regular basis followed and screened for seroconversion due to PRRS virus infection. Sera of animals that were in the process of seroconverting were, during or after seroconversion, used as a source for PRRS virus.

Viruses of the deposited strains I-1387 and I-1388 were isolated from sera of non-clinical cases of PRRS as follows: for growth of the viruses, a 24-hour monolayer of alveolar macrophages was incubated with these sera. The macrophage cell culture was established from lung lavages of SPF piglets with PBS.

The macrophages were washed and incubated with RPMI 1640 medium supplemented with 10% fetal calf serum and antibiotics for 24 hours in 5% $CO_2$ incubator. A small volume of the sera was added to the macrophages. After incubation for 1 h. at 37° C., fresh medium was added and the infected macrophages were further incubated at 37° C. in $CO_2$ atmosphere. Total cytopathic effect (CPE) was apparent after 2–3 days of incubation.

The virus can also be isolated from other sources than the serum, e.g. from heart, tonsils, brain and liver of infected pigs.

EXAMPLE 2

Propagation of PRRS virus

Viruses, isolated as described in Example 1, were inoculated onto a 24-hour monolayer of mammalian cells. After incubation for 1 h at 37° C., the medium was added again and the infected cells were further incubated at 37° C. in $CO_2$ atmosphere. After 2 days, the first signs of CPE became apparent. At day 3 the cells showed complete lysis, which was confirmed by the uptake of trypan blue.

Viable cells do exclude trypan blue dye, as did the non-infected control macrophages. The harvest of this first passage was stored at −70° C. Further passages of this isolate were made by incubation of 1 ml prediluted 1:10–1:100 virus on further macrophages cultures. Total CPE was apparent after 2–3 days of incubation.

Samples of these isolates have been deposited with the CNCM under accession No. I-1387 (strain D) and No. I-1388 (strain C).

The method for the preparation of PRRS viral antigen as described above results in the ability to grow the virus to high titres in vitro.

EXAMPLE 3

Reactivity of PRRS virus strains with monoclonal antibodies

This method was used to check for the reactivity of monoclonal antibodies A27 and A35 against the deposited PRRS viruses. The monoclonal antibodies were diluted 2-fold in microtitration plates containing PRRS virus-infected macrophages. After incubation with FITC-conjugated antibodies, wells were examined for fluorescence.

The IFT test has a deviation of 2 (one dilution step).
Preparation of test system:

Plates were seeded with 100 µl/well swine alveolar macrophages in complete MEM. Plates were incubated in the $CO_2$ incubator.

After at least one night with a maximum of 14 days wells were emptied. Wells were filled with 100 µl virus suspension ($10^5$ $TCID_{50}$/ml, MOI 1:5). Plates were incubated at 37° C. in the $CO_2$-incubator for 24 (±4) hours, emptied and washed once with wash buffer (PBS). Wells were filled with 100 µl cold (−70° C.) 96% ethanol and stored at −70° C.
Immune Fluorescence test procedure:

Just before use the microtiter plates were emptied and washed twice with wash buffer. Monoclonal antibodies were added in duplo (column with infected macrophages and column with negative macrophages) with the desired dilution in PBS buffer. Six serial dilutions were made in PBS buffer with a 2-fold dilution factor (100µl sample+100µl PBS buffer). After dilutions were made the volume in the wells is 100 µl. After 60 minutes at 37° C. the plates were washed two times with wash buffer. To all wells 50µl rabbit anti-Mouse-FITC (1:40) was added. After 60 minutes at 37° C. the plates were washed two times with wash buffer and 50µl of a 50% glycerol in PBS solution at pH 9 was added. Wells were examined for specific fluorescence. Plates were stored at 4° C.

The titre is given as the value of the highest dilution at which virus specific fluorescence is observed. The test is valid if the negative control has no specific fluorescence and the positive control shows specific fluorescence.

All test samples that give specific fluorescence are regarded to be positive.

TABLE 1

|  | I-1140 | I-1387 | I-1388 | I-1389 |
|---|---|---|---|---|
| A35 | + | − | − | + |
| A27 | + | + | + | + |

As can be seen from Table 1, the deposited strains C (I-1388) and D (I-1387) react only with the monoclonal antibody A27.

Contrary to this, the European strain A (deposited with the Collection Nationale de Cultures de Microorganismes (CNCM) of the Institut Pasteur at Paris France under accession number I-1389), which is an attenuated strain derived from virulent strain I-1140 by serial passaging, still reacts with monoclonal antibodies against both A27 and A35.

The highly virulent wild-type strain, deposited with the Collection Nationale de Cultures de Microorganismes (CNCM) of the Institut Pasteur at Paris France under accession number I-1140 on Sep. 6, 1991, reacts with both monoclonal antibodies.

EXAMPLE 4

Lack of pathogenicity of the attenuated strains C and D

An experiment was performed to show that the A35-PRRS virus strains C and D were not pathogenic to pregnant sows and their litters, contrary to the attenuated or wild-type $A35^+$-serotypes.

The sows were inoculated with the live PRRS strains at day 90 of pregnancy.

No difference was found between the number of dead piglets inoculated with strains C or D, and non-infected control sows.

However, the number of dead piglets was significantly different from that of sows inoculated with virus strain A (I-1389) or wild-type PRRS virus strain I-1140.

Pregnant sows, which were negative in the immunofluorescence test (IFT) for PRRS and had farrowed at least once before were used.

| Tested isolates: | |
|---|---|
| Group 1 | PRRS virus strain D |
| Group 2 | PRRS virus strain C |
| Group 3 | PRRS virus strain A |
| Group 4 | PRRS wild-type virus I-1140 |
| Group 5 | Controls, placebo diluent. |

Virus titration:

The infectivity titres of the test strains A, C and D and wild-type virus 110 were determined on macrophages in microtiter plates as described by Wensvoort et al., 1991 and found to be about 6 $^{10}$log $TCID_{50}$ per animal.
Immune fluorescence test:

Sera were diluted (starting dilution 1/10, dilution factor 2) in microtiter plates with (ethanol/fixed) infected macrophages. After incubation with anti-pig IgG-FITC wells are observed for specific fluorescence.
Experimental design Pregnant sows were inoculated with test strains or placebo diluent at day 90 of pregnancy. At day of farrowing blood and colostrum were taken and 8 days after farrowing blood was collected. At day of farrowing the number of mummies, stillbirths, weak piglets that died within a week, and healthy piglets were recorded.

RESULTS

As can been seen in Table 2, the number of dead piglets from the sows inoculated with strain C and D, 0% and 19% respectively, was less than or roughly comparable to the normal reproduction results as found in the placebo controls of Group 4 (14%).

In contrast, 33% dead animals were observed in the group inoculated with the less attenuated $A35^+$ virus strain A.

About 75% dead animals were observed in the group inoculated with the $A35^+$ wild-type virus strain I-1140.

These results prove that the attenuated European vaccine strains of the $A35^-$ serotype are safe vaccine strains which are preferred over attenuated $A35^+$ serotype strains.

TABLE 2

Results of PRRS virus on the litters of inoculated sows

| Sow | Strain | Pigs delivered Dead* | Alive | Total |
|---|---|---|---|---|
| 148 | D | 0 | 9 | 9 |
| 196 | D | 0 | 9 | 9 |
| 230 | D | 0 | 7 | 7 |
| Total | | 0 | 25 | 25 |
| (%) | | (0) | (100) | |
| 8 | C | 2 | 7 | 9 |
| 180 | C | 0 | 6 | 6 |
| 192 | C | 3 | 8 | 11 |
| Total | | 5 | 21 | 26 |
| (%) | | (19) | (81) | |
| Strain A-inoculated (3 sows) | | | | |
| Total | | 15 | 30 | 45 |
| (%) | | (33) | (67) | |
| Strain I-1170-inoculated (3 rows) | | | | |
| Total | | 20 | 15 | 35 |
| (%) | | (75) | (25) | |
| Non-oculated controls | | | | |
| Total | | | | |
| (%) | | 4 | 25 | 29 |
| | | (14) | (86) | |

*Deads include mummies, stillbirths and piglets that died within 7 days after birth.

EXAMPLE 5

Vaccination of fattening pigs with attenuated PRRS virus

In this experiment the efficacy of a PRRSV vaccine against a PRRSV challenge in fattening pigs is demonstrated.

Three groups of animals were used:

| Group | No. animals | Route | Vaccine dose $TCID_{50}$ | Challenge dose $TDIC_{50}$ |
|---|---|---|---|---|
| Group 1 | 11 | ID | $10^{5.6}$ | $10^{4.9}$ |
| Group 2 | 11 | IM | $10^{6.7}$ | $10^{4.9}$ |
| Group 3 | 10 | control | — | $10^{4.9}$ |

Animals were vaccinated at 4–5 weeks of age.

For the intramuscular (IM) application one volume of PRRSV strain D was mixed with one volume of DILUVAC FORTE adjuvant. Each animal was vaccinated with 2 ml.

For the intradermal (ID) application one volume of PRRSV strain D was mixed with one volume of DILUVAC FORTE adjuvant. Each animal was vaccinated with 0.2 ml.

Animals were challenged at 4 weeks after vaccination with PRRSV isolate no. 2. Each animal was challenged intranasally with one ml per nostril. The protection was measured by monitoring body temperatures and challenge virus re-isolation.

Temperatures

Rectal temperatures were measured daily from 1 day before challenge until 7 days after challenge.

FIG. 1 shows the percentage of animals with a temperature above 40.5° C. Only a few vaccinates (ID and IM) became feverish whereas a large number of animals from the non-vaccinated group developed high temperatures.

Challenge virus re-isolation

Blood samples were taken at arrival and weekly until challenge. After challenge blood samples were taken at 2, 4, 6, 10, 13 and 15 days after challenge. Virus titres were determined of the samples. Virus could be re-isolated from most of the controls at several time points. There was a marked difference between the vaccinated pigs and the controls in the presence of PRRSV found in blood (FIG. 2).

Microorganisms

Microorganisms I-1387, 1-1388, 1-1389 and I-1401, I-1402 were deposited with the CNCM of the Institut Pasteur, 28 Rue du Docteur Roux, F-75724 Paris, CEDEK 15 France on 23.12.93 and 09.02.94, respectively.

We claim:

1. A Porcine Reproductive and Respiratory Syndrome (PRRS) virus, of a European serotype, said virus being an attenuated virus reactive with monoclonal antibody A27, as produced by hybridoma A27 deposited with the Collection Nationale De Cultures De Microorganismes (CNCM) of the Institut Pasteur at Paris, France under accession number I-1401, but not reactive with monoclonal antibody A35, as produced by hybridoma A35 deposited with the Institut Pasteur at Paris, France under accession number I-1402.

2. The attenuated PRRS virus according to claim 1, said virus selected from the group consisting of the strains deposited with the Institut Pasteur at Paris, France under accession numbers I-1388 and I-13870 and further passages of I-1388 and I-1387.

3. A vaccine for the protection of pigs against Porcine Reproductive and Respiratory Syndrome (PRSS), comprising an immunogenically effective amount of a live virus according to claim 1 and a pharmaceutically acceptable carrier.

4. The vaccine according to claim 3, comprising $10–10^7$ virus particles.

5. A vaccine for the protection of pigs against Porcine Reproductive and Respiratory Syndrome (PRRS), comprising an immunogenically effective amount of a virus according to claim 1 in an inactivated form and a pharmaceutically acceptable carrier.

6. The vaccine according to claim 5, wherein the virus has a pre-inactivation titre of $10^3–10^{10}$ virus particles.

7. The vaccine according to claim 3, comprising an adjuvant.

8. The vaccine according to claim 5, comprising an adjuvant.

* * * * *